United States Patent
Vergnault et al.

(10) Patent No.: US 8,927,608 B2
(45) Date of Patent: Jan. 6, 2015

(54) COMPOSITIONS COMPRISING AMPHETAMIN AND LISDEXAMFETAMINE

(75) Inventors: Guy Vergnault, Kembs Loechle (FR); Pascal Grenier, Kappelen (FR)

(73) Assignee: Jagotec AG, Muttenz (CH)

( * ) Notice: Subject to any disclaimer, the term of this patent is extended or adjusted under 35 U.S.C. 154(b) by 31 days.

(21) Appl. No.: 13/578,652

(22) PCT Filed: Feb. 16, 2011

(86) PCT No.: PCT/EP2011/052295
§ 371 (c)(1),
(2), (4) Date: Nov. 16, 2012

(87) PCT Pub. No.: WO2011/101374
PCT Pub. Date: Aug. 25, 2011

(65) Prior Publication Data
US 2013/0079415 A1    Mar. 28, 2013

(30) Foreign Application Priority Data

Feb. 16, 2010    (GB) .................................. 1002612.8

(51) Int. Cl.
*A61K 31/16*     (2006.01)
*A01N 37/18*     (2006.01)
*A61K 31/165*    (2006.01)
*A61K 31/137*    (2006.01)

(52) U.S. Cl.
CPC ............. *A61K 31/165* (2013.01); *A61K 31/137* (2013.01)
USPC ............................. 514/626; 514/613; 514/625

(58) Field of Classification Search
CPC   A61K 31/137; A61K 31/165; A61K 2300/00
USPC .................. 514/613, 625, 626, 646, 649, 654
See application file for complete search history.

(56) References Cited

U.S. PATENT DOCUMENTS

| | | | | |
|---|---|---|---|---|
| 6,322,819 | B1 * | 11/2001 | Burnside et al. | 424/494 |
| 6,605,300 | B1 * | 8/2003 | Burnside et al. | 424/452 |
| 6,913,768 | B2 * | 7/2005 | Couch et al. | 424/490 |
| 7,659,253 | B2 * | 2/2010 | Mickle et al. | 514/1.1 |
| 2004/0220277 | A1 * | 11/2004 | Couch et al. | 514/649 |
| 2005/0158384 | A1 * | 7/2005 | Couch et al. | 514/649 |
| 2006/0204575 | A1 * | 9/2006 | Feng et al. | 424/469 |
| 2009/0023712 | A1 * | 1/2009 | Ferger et al. | 514/220 |

FOREIGN PATENT DOCUMENTS

WO    WO 2007/093624 A2    8/2007

OTHER PUBLICATIONS

Krishnan et al., "Multiple daily-dose pharmacokinetics of lisdexamfetamine dimesylate in healthy adult volunteers", 2008, Current Medical Research and Opinion, vol. 24, No. 1, pp. 33-40.*
Brams et al., "Duration of effect of oral long-acting stimulant medications for ADHD throughout the day", 2010, Current Medical Research and Opinion, vol. 26, No. 8, pp. 1809-1825.*
Cowles Brian J: "Lisdexamfetamine for Treatment of Attention-Deficit/Hyperactivity Disorder", Annals of Pharmacotherapy, vol. 43, No. 4, Apr. 2009.
Faraone S V: "Stimulant therapy in the management of ADHD: Mixed amphetamine salts (extended release)",Expert Opinion on Pharmacotherapy 200709 G B LNKD-DOI:10.1517/14656566.8.13. 2127,vol. 8, No. 13, Sep. 2007.
Biederman J. et al.: "Lisdexamfetamine dimesylate and mixed amphetamine salts extended-release in children with ADHD: A double-blind, placebo-controlled,crossover analog classroom study",Biol. Psychiatry,vol. 62, 2007.

* cited by examiner

*Primary Examiner* — My-Chau T Tran
(74) *Attorney, Agent, or Firm* — Mintz Levin Cohn Ferris Glovsky and Popeo, P.C.; Muriel Liberto, Esq.

(57) ABSTRACT

A formulation comprising dexamphetamine and lys-dexamphetamine useful in the treatment of ADHD or fatigue.

21 Claims, No Drawings

COMPOSITIONS COMPRISING AMPHETAMIN AND LISDEXAMFETAMINE

The present invention is concerned with pharmaceutical preparations and their use in the treatment of attention deficit hyperactivity disorder (ADHD).

ADHD is a chronic neuro-behavioural disorder characterised by developmentally inappropriate levels of hyperactivity, impulsivity and inattention. ADHD sufferers have the difficulty regulating their attention, inhibiting their attention to non-relevant stimuli, and/or focusing too intensely on specific stimuli to the exclusion of what is relevant. The clinical symptoms are diverse and may be affected by age, gender, co-morbid conditions and the environment in which a patient finds itself.

ADHD is estimated to affect a relatively small percentage of the school-age population, but it is thought that the number of affected people increases enormously when adolescent and adult populations are taken into consideration as around 30-70% of children with ADHD will continue to exhibit symptoms in adulthood.

Treatment consists of pharmacological therapy and behavioural approaches. Stimulants, including methylphenidate and amphetamine-based agents are the drugs typically employed in pharmacological therapy; although there are non-stimulants drugs which are also available when patients do not respond to stimulants or do not tolerate them.

Amphetamine stimulants were only available in dosage forms having short duration. As a result, multiple daily doses were required to treat patients throughout the day. Multiple daily dosing regimens are, of course, not optimal primarily for reasons of patient compliance, particularly with young children who often have difficulty in swallowing medicaments. Furthermore, complicated dosing regimens can lead to "ups and downs" when the dosages are not taken at correct intervals. Such dosage forms also pose particular difficulties for school children as stimulants, being controlled substances, must be kept in locked containers before and between administrations.

Longer-acting amphetamine stimulant formulations have been formulated to address the problems attendant with the shorter-acting medicaments. Adderall XR is such a longer-acting dosage form. It contains 4 amphetamine salts. The salts are formulated in both immediate release and delayed release forms. The dosage form is said to retain efficacy for up to about 9 hours. Such dosage forms should be capable of effectively managing a patient's symptoms over a school day, but as parents can be faced with the dilemma of either dealing with a difficult child at evening time, or administering a supplemental dosage form close to bedtime and risk the onset of insomnia.

In a more recent development an extended release form similar to that of Adderall XR has been prepared. The product, developed by Shire pharmaceuticals has a code name SPD-465. This formulation contains the same amphetamine salts as Adderall XR, but it is designed to have a duration of action of 14 to 16 hours. However, the product has not been launched and it is thought this is because of problems related to variability and less consistent treatment effects.

The patent literature describes multiple approaches related to the development of amphetamine-based therapies for ADHD. The approaches taken are based on the uses of combinations of amphetamines or their salts, or the use of enantiomers of amphetamines and their salts, in a variety of immediate and/or modified release formulations.

US 2004/0220277 describes a formulation for the treatment of ADHD comprising combinations of enantiomers of amphetamine. More specifically, the formulation comprises particular molar ratios of l-amphetamine and d-amphetamine in free-base or salt form.

US 2004/0059002 discloses a sustained release formulation containing one or more amphetamines and/or their salts. The formulations are useful in the treatment of ADHD.

U.S. Pat. No. 6,605,300 and U.S. Pat. No. 6,322,819 both disclose pulsed delivery systems containing one or more amphetamine salts useful in the treatment of ADHD. Dosage forms overcome the need for multiple dosing to achieve extended release.

WO2004/028509 discloses a sustained release dosage form containing one or more amphetamines and/or salts thereof. The sustained release dosage forms are said to be capable of treating ADHD in the same manner as Adderall XR.

US 2006/0204575 discloses a sustained release dosage form containing two or more amphetamine salts. The formulations are said to reduce variability in bioavailability.

US 2005/0158384 describes a formulation comprising one or more amphetamines in sustained release form. The formulation is said to provide similar blood profiles as Adderall XR and is said to be capable of achieving efficacy over a 10 to 12 hour period.

WO2007/133203 describes a formulation for the treatment of ADHD comprising pharmaceutically active amphetamine salts. The formulation comprises in particular an amphetamine salt adapted for immediate release; and an amphetamine salt formulated with an enteric coating for delayed release. The result is a pulsed delivery system, which is said to mimic the bioavailability of Adderall XR followed by an immediate release amphetamine composition 8 hours later.

Disadvantages attendant with these approaches include variability of dosing, insufficient extension of release and side effects such as insomnia. In addition, a significant drawback with sustained release formulations as compared to immediate release forms adapted for multiple administration resides in the need to use much higher amounts of amphetamine with increased side effects eg, insomnia and loss of appetite, and the abuse potential associated therewith. On the other hand, multiple dosing of immediate release forms carries with it its own disadvantages as have been described above.

An alternative to treatment with sustained and/or immediate release amphetamines has been developed for treatment of ADHD. The treatment is based on the use of a pro-drug of an amphetamine. A product marketed under the trade name Vyvanse is provided in the form of a capsule containing the pro-drug lisdexamphetamine dimesylate in immediate release form containing microcrystalline cellulose, crosearmellose sodium and magnesium stearate as excipients. Lisdexamphetamine dimesylate is a pro-drug of dexamphetamine and consists of a conjugate of lysine and dexamphetamine in its dimesylate salt form. It lacks stimulant properties but is hydrolysed in the gut wall to release d-amphetamine. As it is an inactive material, it cannot be taken nasally, intravenously or in any other way to achieve an illicit stimulant effect. This is considered to be an advantage of this product. Furthermore, the metabolic hydrolysis of the pro-drug takes some time and as such the formulation has an element of in-built controlled release notwithstanding that the product contains only excipients employed in immediate release dosage forms. The product can deliver dexamphetamine over a period of about 8 hours and so it is useful to treat ADHD in paediatric populations (aged 6 to 12), but the extent of its duration is not considered to be sufficient to treat adolescent and adult populations having much longer active days.

Lisdexamphetamine formulations have been described in the patent literature.

US 2005/0038121 describes a formulation for the treatment of ADHD that contains an abuse-resistant lysine amphetamine compound. Extended release can also be achieved due to the metabolic hydrolysis of the lysine amphetamine compound causing a delayed release of the active amphetamine.

WO 2006/121552 describes a similar abuse-resistant formulation containing a lysine amphetamine compound.

US20090137675 discloses pharmaceutical compositions comprising amphetamine pro-drug. Such compositions may be combined with other therapies. Once such therapy is Dexedrine®, which a twice-a-day BID) dosage form of dexamphetamine.

Despite the activity in the prior art, there remains a need for improved formulations with extended profiles, in particular formulations that will deliver amphetamines up to 16 hours or more in order to offer effective treatments not only to children but also to adolescent and adult populations. Improved formulations should also have a fast onset of action and have less inter-variability and more consistent PK profiles. They should have less risk of side-effects such as insomnia and be less prone to abuse. Furthermore, the formulations should exhibit reduced food effect because the rate of release is controlled by metabolism across the gut wall and not by the rate of dissolution, dissolution rates being prone to large fluctuations depending on patients' fed or fasted state. In the same manner, because the release rate is controlled by metabolism and not dissolution rate, one will expect more reproducible effects and reduced occurrence of insomnia.

The present invention provides in one of its aspects a pharmaceutical preparation comprising an amphetamine and a pro-drug of an amphetamine.

The amphetamine may have any stereogenic configuration, such as dextro and levo isomers. The amphetamine may be used in enantiomeric form or as a racemic mixture. The amphetamine may be employed in free-base form or it may be employed as a salt. Pharmaceutically acceptable salts include e.g., non-toxic, inorganic and organic acid addition salts, are known in the art. Exemplary salts include, but are not limited to, 2-hydroxyethanesultonate, 2-naphthalenesulfonate, 3-hydroxy-2-naphthoate, 3-phenylpropionate, acetate, adipate, alginate, amsonate, aspartate, benzenesuifonate, benzoate, besylate, bicarbonate, bisulfate, bitartrate, borate, butyrate, calcium edetate, camphorate, camphorsulfonate, camsylate, carbonate, citrate, clavulariate, cycloperitanepropionate, digluconate, dodecylsulfate, edetate, edisylate, estolate, esylate, ethanesulfonate, fumarate, gluceptate, glueoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, lauryisulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like.

A preferred salt is the mesylate salt or the sulphate salt.

The pro-drug of the amphetamine is comprised of any of the amphetamines referred to above that is bound to a chemical moiety. The chemical moiety can be any moiety that substantially decreases the pharmacological activity of the amphetamine in the bound state as compared to the amphetamine in the free state. Suitable pro-drugs are those described in WO 2006/121552, which is incorporated herein by reference. A preferred pro-drug is L-lysine-d-amphetamine dimesylate (lisdexamphetamine dimesylate).

Pharmaceutical preparations of the present invention containing a combination of amphetamine and a pro-drug of an amphetamine have not been described in the art. Indeed, this combination of drug and pro-drug is counter-intuitive in that the justification in the prior art for using the pro-drug is to obtain a sustained release of amphetamine without the concomitant abuse potential that exists in using a conventional sustained release amphetamine formulation with the amphetamine in its free state.

By combining an amphetamine and a pro-drug of an amphetamine one is able to address the draw backs attendant with prior art formulations. The use of a pro-drug delivers sustained release of amphetamine. At the same time, a small amount of free amphetamine avoids latency in the onset of action after administration. In this manner, fast onset and extended release can be achieved by a single dosage form.

Furthermore, because only a small amount of amphetamine is used in its free state to bridge the time period it takes before the pro-drug is metabolised to release therapeutic blood plasma levels of amphetamine the preparation is less prone to abuse compared with conventional extended release amphetamine formulations.

In prior art extended release formulations, amphetamines are employed in amounts sufficient to deliver therapeutic blood plasma levels over a desired extended period of time. The present invention differs in that it is an extended release formulation that only contains a partial dose of amphetamine in its free state, that is, it contains an amount of amphetamine that is insufficient to cover the whole intended treatment period, which may be 16 hours or even longer.

In a preferred embodiment, the dose of the amphetamine in its free state is about 1 to 50 mg, more particularly 5 to 30 mg.

Similarly, the pro-drug of the amphetamine is partially dosed. As the amphetamine in its free state is contributing a therapeutic effect for a short period of time, the amount of pro-drug needed to sustain blood plasma levels of amphetamine can be lowered compared with conventional dosing of the pro-drugs described in the art. As a consequence of the lower dose, extended release is achieved but the incidence of insomnia onset may be reduced. The amount of pro-drug employed will depend on the nature of the particular pro-drug employed, but should be sufficient to provide 5 to 50 mg of released amphetamine. In a preferred embodiment, employing lisdexamphetamine dimesylate the amount of pro-drug employed is 18 to 180 mg, more particularly 25 to 75 mg.

Dosage forms according to the invention are adapted for once-a-day administration and contain single fractional doses of each of the amphetamine and the amphetamine pro-drug.

In particular, the amount amphetamine employed may be sufficient to provide about ⅓ of the required therapeutic dose of the amphetamine active substance (i.e. amphetamine free base). The amount of amphetamine pro-drug employed may be sufficient to provide about ⅔ of the required therapeutic dose of the amphetamine active substance. So, for example, in the case of the amphetamine being dexamphetamine sulphate and the pro-drug being lisdexamphetamine dimesylate, the amount of dexamphetamine sulphate employed is about ⅙ by weight relative to about ⅚ by weight of lisdexamphetamine dimesylate.

In the case of combinations other than dexamphetamine sulphate and lisdexamphetamine dimesylate, depending on the desired fraction of amphetamine active substance provided by the amphetamine and the amphetamine pro-drug, the skilled person can easily calculate the relative weights of amphetamine and pro-drug needed, having regard to the amphetamine counter-ion (if any) and the nature and structure of the pro-drug employed.

In another aspect of the present invention there is provided a pharmaceutical preparation as defined above that is effective to provide a substantially complete release of both amphetamine and amphetamine pro-drug in about 0.5 to 1 hours in-vitro in a Type II USP dissolution apparatus 900 ml 0.1 HCl at 37 degrees centigrade and 50 rpm.

In another aspect the pharmaceutical preparation as hereinabove described provides a dissolution of the amphetamine of about 5 to 30% within 0.5 hours, about 30 to 70% within 1.0 hours and not less than 80% within 1.5 hours when measured in a Type II USP dissolution apparatus, 900 ml 0.1 HCL at 37 degrees centigrade and 50 rpm.

In another aspect the pharmaceutical preparation as hereinabove described provides for the dissolution of the amphetamine pro-drug of about 5 to 50% within 5 min, about 20 to 70% within 10 min and not less than 80% within 20 min when measured in a Type II USP dissolution apparatus 900 ml 0.1 HCl at 37 degrees centigrade and 50 rpm.

Procedures for carrying out in-vitro dissolution tests are well known in the art. Typically a dissolution apparatus may be set by programming the temperature, rotation and run time at 37 degrees centigrade, 50 rpm and 24 hours. Typically 900 ml of dissolution medium is placed in each of six vessels of the dissolution apparatus. The apparatus is assembled and the dissolution medium is equilibrated to 37 degrees and the thermometer is removed. One unit dosage form is placed in each of the six vessels. Rotation of the paddle is started at the speed of 50 rpm for 24 hours. Aliquots (each of 6 ml) are withdrawn, and successively replaced with equal volumes of fresh dissolution medium, at the desired interval periods from each of the six vessels.

The amount of dissolved amphetamine or amphetamine pro-drug can be determined conventionally by HPLC. Quantification can be effected by comparison of HPLC peak height (or area) with the peak height (or area) taken from a standard plot of concentration vs. peak height (or area) for standards of known concentration.

Test preparations are separately injected into the chromatograph after filtering through 0.45 [mu]m membrane filter. Chromatograms are recorded and the peak responses of the test peak are compared in terms of area with a standard. The quantity of amphetamine or pro-drug released in percent (%) can then be calculated.

The present invention provides in another of its aspects a dosage form as hereinabove described, which provides a mean time to peak plasma concentration (Tmax) of amphetamine, which occurs at about 1 to 12 hours after oral administration to a human subject. The Tmax values may vary within this range. In particular, Tmax may be reached within 1 to 4 hours. Alternatively, if the dosage form releases its dose with a lag time, as is more fully described below, Tmax may be achieved in a longer time frame, e.g. from 6 to 12 hours.

The invention provides in another of its aspects a dosage form as hereinabove described, which provides a mean $AUC_{0-48\ hr}$ of amphetamine from about 130 to 1400 ng·hr/ml (based on a dose of amphetamine and amphetamine pro-drug equivalent to 5 to 50 mg of amphetamine).

The amphetamine exhibits substantial dose proportionality with respect to AUC and $C_{max}$. For example, a 30 mg dose of amphetamine will provide a mean $AUC_{0-48}$ of about 600 to 900 hr·ng/ml. Furthermore, as there is substantial dose proportionality, the skilled person is able to obtain Cmax and AUC for other doses by extrapolation or interpolation from the measured values. By way of further example a 10 mg dose of amphetamine will provide a mean $AUC_{0-48}$ of about 200 to 300 hr·ng/ml.

The pharmacokinetic parameters $T_{max}$, $C_{max}$ and AUC are terms well known in the art. $T_{max}$, $C_{max}$ and AUC can be obtained by plotting blood plasma concentrations of a drug (Y-axis) against time (X-axis). $C_{max}$ is the observed maximum of this plot and $T_{max}$ is the time to the observed $C_{max}$. $AUC_t$ corresponds to the area under the curve up to certain sampling points (or extrapolated in some cases) and reflects the bioavailability of a drug for a given route of administration. These values are typically measured as mean values.

The term "mean" as used herein in relation to these pharmacokinetic parameters represents the arithmetic mean value measure across a patient population (usually at least 10 patients).

The pharmaceutical preparations as hereinabove described are adapted for once-a-day administration. They can deliver therapeutic efficacy over extended periods of time, in particular up to 18 hours, e.g. 12 to 16 hours.

Such extended release renders the preparations suitable not only for use with the paediatric population, but also with adolescent and adult populations having typically longer active days, which is currently an unmet need.

The pharmaceutical preparations of the present invention may be adapted to release amphetamine and pro-drug according to a modified release profile. Modified release dosage forms are defined by the USP as those whose drug release characteristics of time course and/or location are chosen to accomplish therapeutic or convenience objectives not offered by conventional immediate release dosage forms. The term modified release is often used synonymously with terms such as "controlled release" and also "sustained release" or "extended release". Modified release however, also includes the release of a drug (including immediate release of drug) after a lag-time after administration orally, during which lag-time no, or substantially no, drug is released.

A lag time may be as a result of the response of a dosage form to change in external physiological media, for example, a change in pH, a change in enzymatic concentration and the like. Alternatively, a lag time may be time-dependent and independent of changes physiological media. For example, a lag time might derive from the time taken for a drug to migrate across a coating, and the duration of the lag time will merely be a function of the thickness and the porosity of the coating.

A pharmaceutical preparation adapted to release drugs after a pre-determined lag-time after administration orally might be particularly useful if it is desired to administer a drug before bedtime in order that it releases the drug upon awakening in order to arrest symptoms occurring immediately upon wakening. Such an embodiment might be particularly useful in paediatric populations whose hyperactivity may commence substantially immediately upon wakening. Such an embodiment might also be particularly useful in patients suffering fatigue, in particular cancer fatigue, the debilitating effects of which often can occur immediately upon wakening and which is not relieved by rest and sleep.

In a pharmaceutical preparation adapted to release after a pre-determined lag-time, it is preferred if the lag-time is a time dependent lag-time that is independent, or substantially so, of any changes in the physiological environment surrounding the preparation, such as a change in pH or temperature or enzymatic conditions. As pH and enzyme concentration can be somewhat affected by food intake, such a preferred embodiment should release drug substantially absent of a food effect. The term "food effect" well known in the art and is an expression to describe the variance in bio-availability of drug substances between fed and fasted states.

A suitable lag-time for a pharmaceutical preparation of the present invention is 5 to 8 hours.

As stated herein, during a lag time none, or substantially none, of a drug is released. By the phrase "none or substantially none" as it relates to the release of a drug from a preparation described herein, is meant that any release is in such small amounts that therapeutically effective blood plasma levels of amphetamine are not reached. In particular, in so far as any dose is released, it is no more than about 10%, still more particularly no more than 5%, still more particularly no more than about 1%.

Pharmaceutical preparations adapted to deliver with a lag-time can, depending on the length of that lag-time, be administered before bedtime. Such a preparation has the attendant advantages described above associated with the release of drug shortly before morning wakening.

The term "morning" as it is used herein refers to the period early in the day after a patient has awakened after overnight sleep, generally between 6 a.m. and 10 a.m.

Accordingly, in another aspect of the invention there is provided a pharmaceutical preparation as hereinabove described adapted for administration orally before bedtime.

By "bedtime" as this term relates to the dosing schedule described above, is meant a period immediately before a subject retires to bed for sleep. This period may differ from subject to subject, and substantially when comparing children's sleeping habits with adults. More particularly, bedtime is between about 7 pm to midnight, still more particularly about 7 to 9 pm for children and between 10 pm and midnight for adults.

Whether the pharmaceutical preparation is adapted to release after a lag-time or not, it is preferred that the pharmaceutical preparation is adapted for immediate release of the amphetamine in order to ensure that the patient receives therapeutic plasma levels of amphetamine as rapidly as possible after administration.

The pharmaceutical preparation might also be adapted for immediate release of the amphetamine pro-drug. However, it is also contemplated that the pharmaceutical preparation is adapted for controlled release of the pro-drug. The precise form of the pharmaceutical preparation chosen to deliver the pro-drug will depend upon the desired release profile and it is well within the purview of the skilled person to select an appropriate formulation principle with the desired target release profile in mind.

In a particular embodiment the pharmaceutical preparation is formulated to release the amphetamine pro-drug in a sustained release. In conventional formulations containing lisdexamphetamine in immediate release form, as the formulation releases the pro-drug into the gastro-intestinal tract it begins to hydrolyse to release dexamphetamine. If, in a pharmaceutical preparation this process is delayed slightly by formulating the pro-drug in a sustained release form, the onset of therapeutic blood plasma levels will be delayed. If this delay is adapted such that the time to minimum therapeutic concentration of amphetamine released from the pro-drug coincides with the time at which immediate release amphetamine concentrations decay below a therapeutic level, then one will be able to employ lower amounts of pro-drug for a given duration of extended release.

In the manner described above, pharmaceutical preparations of the present invention can deliver amphetamine in a fast-acting manner and for extended duration to meet the therapeutic needs in a convenient once-a-day form.

Accordingly, in another aspect of the invention there is provided a pharmaceutical preparation as hereinabove described for once-a-day administration oral administration. Amphetamine and pro-drug can be delivered in a sequential, simultaneous or separate manner.

The pharmaceutical preparations of the present invention are intended for administration through the oral route. As such, they may take any form conventional in the art, that is, they may be in the form of tablets, capsules, caplets, powders, pellets, granules, syrups and the like.

The pharmaceutical preparations may be configured in any suitable manner having regard to the particular release profile that is sought. Pharmaceutical preparations of the present invention may vary in release rate characteristics from immediate release to controlled release, or a mixed profile of immediate release and controlled release. Release may be continuous or pulsatile.

The pharmaceutical preparation may be monolithic and contain both the amphetamine and the pro-drug in a common immediate release matrix, or the matrix may be adapted for controlled release.

Alternatively, the dosage form may contain multiple discrete phases, one or more of which will contain amphetamine, and one or more of which will contain pro-drug of amphetamine. The phases may be adapted for immediate release or controlled release. The different phases may be in the form of layers of a multi-layered tablet in which case they may be arranged sandwich-like or in a concentric arrangement.

Alternatively, there may be a core phase in which is dispersed one or more discrete phases, again with each phase being adapted for controlled or immediate release.

Still further, the pharmaceutical preparation may be in the form of multi-particulates or mini-tablets or beads each adapted for a particular release profile. Such multi-particulates or mini-tablets or beads can be contained in a sachet or in a capsule. The skilled person will appreciate that there is a wide variety of possible configurations for the pharmaceutical preparations and the particular configuration will depend on the release profile sought.

In yet another aspect of the present invention there is provided a method of treating attention deficit hyperactivity disorder (ADHD) in a patient in need of such treatment comprising the step of providing said patient with a pharmaceutical preparation as hereinabove defined.

In a particular embodiment, in a method described above the patient is a child aged 6 to 12.

In another particular embodiment, when the patient is a child, the method comprises the step of administering at bedtime, a pharmaceutical preparation as described above adapted to release after a lag-time.

In another particular embodiment, in a method described above the patient is an adolescent or an adult.

In yet another aspect of the present invention there is provided a method of treating fatigue comprising the step of administering to said patient a pharmaceutical preparation as hereinabove defined.

In a particular embodiment in a method described in the preceding paragraph the fatigue is cancer fatigue.

In another particular embodiment, there is provided a method of treating cancer fatigue, comprising the step of administering to a patient at bedtime, a pharmaceutical preparation as described above adapted to release after a lag-time.

In order to facilitate the preparation of pharmaceutical preparations described above there is provided, in a further aspect of the present invention, a process for the preparation of a pharmaceutical preparation useful in the present invention.

Pharmaceutical preparations may be prepared by treating the amphetamine and pro-drug with one or more pharmaceutically acceptable excipients, and formulating the resultant mixture into the desired form using techniques well known in the art.

Techniques and compositions for making tablets (compressed and molded), capsules (hard and soft gelatin) and pills are also described in Remington's Pharmaceutical Sciences, 18th ed. Arthur Osol, 1553-93 (1990), which is incorporated herein in its entirety for this purpose.

Techniques include melt-granulation, wet granulation, dry blending, dry granulation, co-precipitation, extrusion and melt extrusion.

When the preparation is in the form of a tablet, the tablet can be prepared by either direct compression, dry granulation (slugging and roller compaction), or by wet granulation. Wet granulation techniques may be either aqueous or non-aqueous. Non-aqueous solvents may be selected from a group comprising ethanol, isopropyl alcohol, acetone or methylene chloride.

Tablets may be made by compression methods by the application of high pressures to powders or granulates utilizing steel punches and dies. In this manner a wide variety of shapes, sizes and surface markings can be formed depending on the size and design of the punches and dies employed. On an industrial scale they may be produced using rotary presses, e.g. a Manesty press, Liverpool, United Kingdom or a Korsch and Kilian press, Berlin, Germany. Presses generally operate at pressures of about 1000 to about 5000 kg/cm$^2$.

Dry granulation (formed by slugging or roller compaction) involves the compaction of powders at high pressure into large tablet compacts. Granulates may also be formed by pressing/pushing powders between rollers of a chilsonator to form thin and dense ribbons. These compacts are then milled and screened to form granulates of the desired particle size.

Wet granulation is a technique widely employed in the art and comprises the steps of i) weighing and blending pharmaceutical ingredients and excipients; ii) preparing a damp mass from the ingredients and excipients; iii) screening the mass into pellets or granules; iv) drying the granulate; v) sizing the granulate by screening; vi) adding lubricant as appropriate and blending; and vii) tabletting by compression.

Should coating of the pharmaceutical preparations be required, this can be achieved using conventional coating techniques such as press coating, spray coating, pan coating or air suspension coating techniques generally known in the art. All of the techniques discussed above are described in detail in Ansel's Pharmaceutical Dosage Forms and Drug Delivery Systems, Chapter 7, Seventh Edition, 1999 (Lippincott Williams & Wilkins), which is herein incorporated by reference for this purpose.

Excipients may be employed in the pharmaceutical preparations to optimise the bulk properties of the preparation and to affect the desired release profile. These excipients typically include diluents or fillers, which add bulk to enable formulations of a desired size to be prepared; binders or adhesives, which promote the adhesion of the particles of a formulation to maintain the integrity of the dosage form; disintegrants or disintegrating agents, which promote the break-up of the dosage than after ingestion to make the ingredients more readily available; anti-adherents, glidants or lubricants, which enhance the flow of the tabletting materials, for example into tablet dies, prevent sticking of the formulation to tablet-making machinery; and miscellaneous adjuvants such as colourants and flavourants.

Suitable diluents include pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel grades, PH101 PH102, PH112, PH113, PH200, PH300, PH301, CE 15, HFE 102, PH 102 SCG; lactose such as lactose monohydrate, lactose anhydrous, and Pharmatose DCL 21; dibasic calcium phosphate such as Emeompress, Calipharm, Ditab; mannitol; starch, modified starches; sorbitol; fructose; sucrose; and glucose. Diluents are carefully selected to match the specific requirements of the preparation. The diluent is preferably used in an amount of 10% to 90% by weight, more particularly 50% by weight, of the pharmaceutical preparation.

Suitable lubricants and glidants, including agents that act on the flowability of the powder to be compressed are, for example, colloidal silicon dioxide such as Aerosil 200, Cab O Sil; talc; stearic acid, magnesium stearate, calcium stearate, sodium stearyl fumarate, polyethylene glycol and sodium lauryl sulphate. The lubricant is preferably used in an amount of 0.5 to 2% by weight, in particular 1% by weight, of the pharmaceutical preparation.

Suitable binders include polyethylene glycols such as PEG 6000; cetostcaryl alcohol; cetyl alcohol; polyoxyethylene alkyl ethers; polyoxyethylene castor oil derivatives; polyoxyethylene sorbitan fatty acid esters; polyoxyethylene stearates; poloxamers; waxes, alginic acids and salts thereof; HPC; HPMC; methylcellulose; maltodextrin and dextrin; povidone; gums; starch and modified starches. The binder preferably may be used in an amount of 2 to 10% by weight, more particularly 5% by weight, of the dosage form.

Suitable disintegrants include sodium starch glycolate, such as Explotab, crospovidone such as Kollidon CL, polypiasdone XL, sodium carboxymethylcellulose, sodium croscarmellose such as AcDiSol, and starch. The disintegrant preferably may be used in an amount of 2 to 10% by weight, more particularly 5% by weight, of the dosage form.

If a particularly rapid immediate release is required, with or without a lag time, the preparation may comprise a surface-active agent such as sodium lauryl sulfate, sodium monoglycerate, sorbitan monooleate, polyoxyethylene sorbitan monooleate, glyceryl monostearate, glyceryl mono-oleate, glyceryl monobutyrate, any one of the Pluronic line of surface-active polymers, or any other suitable material with surface active properties or any combination of the above.

Surface active materials may be present in the preparation in amounts of 0.1 to 10% by weight.

The total excipients employed may be present in the dosage form in amounts of 1.00 to 99.99% by weight.

Additional examples of pharmaceutically acceptable carriers and excipients that can be used to formulate the preparations are described in the Handbook of Pharmaceutical Excipients, American Pharmaceutical Association.

If it is desired to release amphetamine or the pro-drug with a controlled release as opposed to an immediate release then the preparation, in addition to any of the excipients described above, a release rate controlling agent should be employed.

The term controlled release as it relates to a pharmaceutical preparations of the present invention refers to a that preparation, or a part thereof, comprising a phase that is adapted to release a dose of amphetamine or pro-drug within a certain time to accomplish a therapeutic objective not possible using a conventional immediate release phase.

The term "release rate controlling agent" includes any agent or agents that alone or in combination, optionally together with other excipients, controls the rate of release of a drug in terms of duration in order to give a therapeutic effect not possible with a conventional immediate release formulation, and includes hydrophilic polymers, hydrophobic polymers or mixtures thereof, or copolymers thereof, or mixtures of these polymers and copolymers.

The release controlling agent may be in a matrix in which a drug is dissolved or dispersed. Alternatively, the release controlling agent may be in a layer or coating surrounding a matrix containing a drug. Still further, it may be employed in a matrix and a coating. When the release controlling agent is in the layer or coating, the matrix may also contain a release controlling agent, or it may be adapted for immediate release, or a mixture of both.

Examples of release-rate controlling agents to be used in this invention include hydroxyalkylcellulose, such as hydroxypropylcellulose and hydroxypropylmethylcellulose (hypromellose); poly(ethylene)oxide; alkylcellulose such as ethycellulose and methylcellulose; carboxymethylcellulose; hydrophilic cellulose derivatives; polyethylene glycol; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly(vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

The release-rate-controlling agent may include a hydroxypropyl methylcellulose (HPMC), a hydroxypropyl cellulose (HPC), a poly(ethylene oxide), an ethylcellulose or a combination thereof, in particular present in an amount of 5 to 90% based on the weight of the pharmaceutical preparation.

Preferred types of HPMC for use in accordance with the invention are those sold under the trademark Methocel (Dow Chemical Co.). Suitable Methocels include the K grades such as Methocel K 15M, Methocel K 100M, Methocel K 100LV and Methocel K 4M. Other suitable Methocels include the E, F and J grades.

As HPCs there can be employed those sold under the trademark Klucel (Hercules, Inc.) or equivalents. Suitable Klucels include Klucel LF, Klucel JF, Klucel GF, Klucel MF and Klucel HF.

As poly(ethylene oxide)s there may be mentioned those sold under the trademark Sentry Polyox (Union Carbide Corp.) or equivalents. Suitable Polyoxs include the Polyox WSR grades such as Polyox WSR Coagulant, Polyox WSR-301, Polyox WSR-303, Polyox WSR N-12K, Polyox WSR N-60K, Polyox WSR-1105, Polyox WSR-205 and Polyox WSR N-3000.

As ethylcelluloses for use in accordance with the invention there can be mentioned those sold under the trademark Ethocel (Dow Chemical Co.) or equivalents.

The hydroxypropylmethylcelluloses preferably have a viscosity (2 wt % solution at 2O.degree. C.) of about 5 to 100,000 mPa·s, preferably 4,000 to 100,000 mPa·s. Especially suitable are Methocel K types or their equivalents. The hydroxypropylcelluloses used according to the invention preferably have a number average molecular weight of about 80,000 to 1,150,000, more preferably 80,000 to 600,000.

Poly(ethylene oxide) preferably have number average molecular weights of about 100,000 to 7,000,000, more preferably 900,000 to 7,000,000. Especially suitable is Polyox WSR Coagulant, which has a molecular weight of 5,000,000.

The ethylcelluloses used according to the invention preferably have a viscosity of about 3 to 10 mPa·s, more preferably 7 to 100 mPa·s.

Additional example of materials or excipients that may form part of a controlled release matrix are contained in Remingtons Pharmaceutical Sciences, 18th ed. Mack Publishing Co., Easton, Pa., 1990, p. 1684-1685), which is incorporated herein in its entirety for this purpose.

Pharmaceutical preparations of the present invention may be coated with a non-functional coating or coatings, that is, a coating that does not influence lag time or release rate. Such coatings include those employed to achieve an aesthetic effect (e.g. an attractive colour or pleasant taste) or information effect, e.g. a coating may be coloured to act as a visual cue for a patient identification of a medicament. Coatings may also be over written with information relating to the dosage, or they may elicit a handling effect, e.g. a smooth coating for ease of swallowing, or a stability effect, e.g. a moisture or light barrier during storage.

Should the pharmaceutical preparation be adapted to release the amphetamine and/or pro-drug with a lag-time, as stated above, any formulation principle used to achieve a lag-time could be employed. However, a preparation having a time-dependent lag-time is preferred.

Particular pharmaceutical preparations adapted to release with a time-dependent lag-time may be in the form of press-coated tablets.

A press-coated tablet typically consists of a core containing drug and a coating, formed by pressing, surrounding the core. The core may be configured in any suitable manner. It can be monolithic or multi-phase and be adapted for immediate release or modified release or both as described above. The coating is adapted to provide a barrier to the egress of the beta 2 adrenergic receptor agonist contained in the core until the lag time has expired.

Preferably, the coating comprises one or more water insoluble or poorly soluble hydrophobic excipients. Preferably these excipients are selected from fatty acids or their esters or salts; long chain fatty alcohols; polyoxyethylene alkyl ethers; polyoxyethylene stearates; sugar esters; lauroyl macrogol-32 glyceryl, stearoyl macrogol-32 glyceryl, and the like.

Other excipients that provide a hydrophobic quality to coatings may be selected from any waxy substance known for use as tablet excipients. Preferably they have a HLB value of less than 5, and more preferably about 2. Suitable hydrophobic agents include waxy substances such as carnauba wax, paraffin, microcrystalline wax, beeswax, cetyl ester wax and the like; or non-fatty hydrophobic substances such as calcium phosphate salts, e.g. dibasic calcium phosphate.

Coatings comprising the aforementioned materials provide for a lag time by acting as a barrier to the ingress of a physiological medium. Once the medium crosses the coating and enters the core, it may cause the matrix to hydrate and expand, for example by swelling, gelling or effervescing, thereby breaking it open to expose the core and permit the release of drug from the core. In this way, the coating exerts no, or substantially no, influence over the release rate after expiry of the lag time. Preferably coating ingredients include calcium phosphate salts, glyceryl behenate, and polyvinyl pyrollidone, or mixtures thereof, and one or more adjuvants, diluents, lubricants or fillers as described hereinabove.

Preferred components in the coating are as follows, with generally suitable percentage amounts expressed as percentage weight of the coating.

Polyvinyl pyrrolidone (Povidone) is preferably present in amounts of about 1 to 25% by weight or the coating, more particularly 4 to 12%, e.g. 6 to 8%.

Glyceryl behenate is an ester of glycerol and behenic acid (a C22 fatty acid). Glyceryl behenate may be present as its mono-, di-, or tri-ester form, or a mixture thereof. Preferably it has an HLB value of less than 5, more preferably approximately 2. It may be present in amounts of about 5 to 85% by weight of the coating, more particularly from 10 to 70% by weight, and in certain preferred embodiments from 30 to 55%.

Calcium phosphate salt may be the dibasic calcium phosphate dihydrate and may be present in an amount of about 10 to 90% by weight of the coating, preferably 20 to 80%, e.g. 40 to 75%.

The coating may contain other common tablet excipients such as fillers, binders and the like, commonly used in forming solid oral dosage forms, such as those described above.

The coating thickness surrounding the core will influence the lag time, and can also affect the rate of drug release thereafter depending on the nature of the coating materials selected.

Press-coating provides a particularly effective means of controlling coating thickness, and therefore controlling the lag time.

Press-coating is particularly advantageous as one can control coat weight, diameter of die and size of core to achieve a precisely defined minimum coating thickness at selected points on the dosage form. Ingress of a physiological medium across the coating at these points will determine the time period for the medium to reach the core and hydrate it, and the lag time may be controlled in this manner.

The thickness of the coating in the plane orthogonal to the direction of compression of the dosage form is carefully selected as it is in this plane that the coating is preferentially infiltrated by the physiological medium and it is in this plane that the tablet will eventually rupture, thereby determining the lag time, after which the contents of the core are released.

The formulator can influence the thickness of the core in this plane and thereby control the lag time. It is important that the coating thickness is identical or substantially so in this plane.

The thickness of the coating in this plane should be about 0.5 to 5 mm, more particularly 1 to 3 mm.

Press-coated dosage forms are generally formed by placing a portion of a powdered coating material in a die and tamping the powder into a compact form using a punch. A preformed core is then deposited onto the compacted coating material before the remainder of the coating material is introduced into the die and compression forces are applied to form the coated dosage form. To ensure that the core is placed on the tamped coating material and to ensure it's correctly positioned in order that the coating thickness will be uniform about the orthogonal plane, it is preferable to employ means for positioning the core in relation to the coating material in a die. Typically such means may be provided by a pin punch or a double punch. A pin punch is a punch that has a convex surface that contacts the coating material to leave a small depression or hollow in the tamped coating material. Thus, when the core is placed into the die on the tamped material, it sits in the depression or hollow and its correct geometry is assured in the final tablet form.

In one embodiment, a cup formed by a pin or double punch is filled with a blend containing the drug substance and then a press coated tablet is subsequently formed.

When selecting coating materials for press-coated tablets, it is preferred not to employ materials that are swellable or gellable. Typical of such materials are cellulose ethers or cellulosic derivatives such as hydroxyalkyl celluloses, e.g. hydroxypropylmethylcellulose, or carboxyalkylcelluloses and the like. Such materials tend to form gels which exert a release-controlling effect by forming an erodible barrier through which drug substance may diffuse. Such materials tend to give unreliable lag times and should be avoided in amounts that exert a release-controlling effect. Their release-controlling properties are usually evident when they are employed in amounts of about 10% or greater. Preferably therefore, if any of the aforementioned materials are employed as coating materials they should only be used in small amounts, e.g. less than 10%, more particularly less than 5%, still more particularly less than 1%.

Dosage forms described above may be over-coated with a pharmaceutically acceptable film-coating, for aesthetic purposes (e.g. including a colourant), for stability purposes (e.g., coated with a moisture barrier), for taste-masking purposes, or for the purpose of protecting unstable drug substances from aggressive media, e.g. enteric-coatings.

Press-coated tablets may be prepared by techniques known in the art. A press-coating may be formed by compression using any of the press coaters known in the art. Alternatively, dosage forms may be prepared by granulation and agglomeration techniques, or built up using spray drying techniques, followed by drying.

During compression of the coating around the core, the coating material around the core in the direction of compression is relatively highly compacted and dense. On the other hand, the coating material disposed in the plane orthogonal to the direction of compression is subjected to relatively lower compaction forces and is relatively less dense as a result. Accordingly, the material in this plane is relatively porous and permissive towards the ingress of a physiological medium. Because of the slightly less dense nature of the coating material in this plane, and because the formulator has the latitude to influence the coating thickness, the rate of ingress of the aqueous medium through the coating in this plane can be closely controlled.

Once a physiological medium contacts the core, the core may react by hydrating and swelling and/or gelling or effervescing thereby to break open the coating generally along the direction of ingress of the aqueous media to form to essentially two hemispheres of coating material that may remain conjoined. In this opened form, the tablet, once ruptured may have the appearance of an opened shell, or the two hemispheres of the coating may become completely detach from each other. The reaction of the core material to the presence of the aqueous medium is likewise in part responsible for controlling the release of the beta 2 adrenergic receptor agonist from the core.

The hardness of the tablet is preferably at least 40 Newtons, e.g. 40 to 80 Newtons, and more particularly 60 to 75 Newtons. Hardness may be measured according to a process described in The European Pharmacopoeia 4, 2.9.8 at page 201.

Tablets having an hardness within this range are mechanically robust to withstand forces generated in the stomach, particularly in the presence of food. Furthermore, the dosage forms are sufficiently porous about the plane orthogonal to the direction of compression to permit ingress of physiological media to the core at an appropriate rate to achieve the lag times referred to herein.

The invention provides in another aspect, a method of forming press-coated tablets as herein above described. They may be formed on conventional press coating equipment. Typically such equipment is composed of a series of die are arranged on a rotating platform. The dice are removably mounted in the platform such that differently sized dice may be employed as appropriate. Each die is hollow to receive a lower punch. The punch is positioned, within the die such that the upper surface of the punch and the inner surface of the die define a volume for receiving a precise amount coating material. Once loaded, the platform is rotated until the die is positioned under an upper punch. The upper punch is then urged down onto the coating material under a defined compression force and the coating material is pre-compressed or tamped between the upper and lower punch. A pre-formed core is then fed into die to rest on the tamped coating. Conventional press coating apparatus may be equipped with centering devices that enable cores to be positioned both vertically and radially. This might be achieved by a tamping process, whereby an initial amount of coating material is placed in a die and is tamped with a shaped punch, such as a pin punch, that leaves an indentation in the coating material in which to receive a core. Thereafter, in a second filling operation, a precise amount of coating material is fed into the die to cover the core, and an upper punch compresses the coating material with a defined compaction force to form press-coated tablets. The compression force applied during the tamping process is relatively light and is just sufficient to provide abed of coating material to receive the core and to prevent movement of the coating material as a result of centrifugal force. Subsequent compression to form the dosage form may be adjusted to give a requisite hardness.

Preferably, this compression force is 400 kg, although this may be adjusted by +/−30% in order to give tablets of the required hardness.

The amount of coating material fed into the die can be precisely defined having regard to the density of the coating material, as can the dimension of the die to ensure after compression that the dosage form is formed with the required coating thickness, particularly about the plane orthogonal to the direction of compression. Should it be necessary to change the thickness of the coating, die of appropriate internal dimensions may be placed in the rotating platform, and the amount of coating material fed into the die may be adjusted accordingly.

Suitable rotary tablet machines having high process speeds are known in the art and need no further discussion here.

Cores may likewise be formed using a conventional rotary tablet machine. Cores are preferably compressed under compression forces sufficient to provide cores having a hardness of about 60 Newtons at least, e.g. 50 to 70 Newtons. Cores having hardness in this range give desired release characteristics. If desired, the cores can be formed at the same time as the press coated tablets are produced. In such case, one might employ a Manesty Dry Cota. Such, a press consists of two side-by-side and inter-connected presses where the core is made on one press before being mechanically transferred to the other press for compression coating. Such equipment and techniques for making dosage forms using such equipment are known in the art and no more needs to be said about this here.

Cores are preferably formed according to wet granulation techniques generally known in the art. In a typical procedure, core materials are sieved and blended. Granulating fluid, typically water is then added to the blend and the mixture is homogenized to form a granulate, which is then sprayed dried or dried on a fluid bed drier to obtain a granulate with requisite residual moisture. Preferably the residual moisture content is from about 0.4 to 2.0% by weight. The granulate is then sized by passing it through screens of desired aperture. At this stage, any adjuvants are sized and added to the granulate to form the core composition suitable for compression. The skilled person will appreciate that a coating composition can be formed in an analogous manner.

Press-coated tablets of the invention could also be manufactured as one-step dry coated tablets with a double punch tooling, using for example a Kikusui Seisakusho press, Kyoto Japan.

There now follows a series of examples that serves to illustrate the invention.

EXAMPLE 1

| | |
|---|---|
| Dexamphetamine sulphate USP/NF | 10 mg |
| Lisdexamphetamine mesylate | 30 mg |
| Kollidon 30 | 10 mg |
| Avicel PH101 | 100 mg |
| AcDiSol | 10 mg |
| Syloid 244 | 1 mg |
| Magnesium stearate | 2 mg |
| Total tablet weight | 163 mg |

Dexamphotamine, lisdexamphetamine, Avicel PH 101, Kollidon 30 and one third of AcDiSol are mixed together in a high shear mixer, water is added until cohesive granules are formed. These granules are then dried in a fluid bed drier until LOD<2%, is reached. After dry sizing on a cone mill, final blend is prepared by mixing the obtained granules with the rest of AcDiSol, Syloid and Magnesium Stearate in a diffusion mixer.

Tablets of 7.5 mm diameter are obtained by compression of the final blend on a rotary tablet press.

EXAMPLE 2

| A bilayer tablet | |
|---|---|
| Layer 1 granules: 100 mg | |
| Dexamphatamine sulphate USP/NF | 10 mg |
| Kollidon 30 | 5 mg |
| Avicel PH 101 | 78.5 mg |
| AcDiSol | 5 mg |
| Syloid 244 | 0.5 mg |
| Magnesium stearate | 1 mg |
| Layer 2 granules: 182.25 mg | |
| Lisdexamphetamine mesylate | 50 mg |
| Plasdone K29-32 | 10 mg |
| Avicel PH 101 | 30 mg |
| Glyceryl behenate | 30 mg |
| Methocel K100M | 60 mg |
| Syloid 244 | 0.75 mg |
| Magnesium stearate | 1.5 mg |

Manufacturing process layer 1:Dexamphetannine, Avicel PH 101, Kollidon 30 and one third of AcDiSol are mixed together in a high shear mixer, water is then added until cohesive granules are formed. These granules are then dried in a fluid bed drier until LOD<2% is reached.

After dry sizing on a cone mill, final blend is prepared by mixing the obtained granules with the rest of AcDiSol, Syloid and Magnesium Stearate in a diffusion mixer.

Manufacturing process layer 2: Lisdexamphetamine, Avicel PH 101, Plasdone K29-32, Methocel K100M: and glyceryl behenate are mixed together in a high shear mixer, water is then added until cohesive granules are formed. These granules are then dried in a fluid bed drier until LOD<2% is reached.

After dry sizing on a cone mill, final blend is prepared by mixing the obtained granules with the rest of AcDiSol, Syloid and Magnesium Stearate in a diffusion mixer.

Bilayer tablets having a total weight of 282.25 mg are obtained by compression of the final blends on a rotary bilayer tablet press equipped with 9 mm diameter tooling.

EXAMPLE 3

| Immediate release pellets IRP: | |
| --- | --- |
| Non pareil sugar spheres 30/35 mesh USP/NF | 78% |
| Pharmacoat 603 | 1% |
| Dexamphetamine sulfate USP/NF | 15% |
| Opadry II | 4% |

In a fluid bed drier fitted with Wurster insert, a suspension of dexamphetamine sulphate and Pharmacoat 603 is sprayed onto non pareils spheres. When the whole amount of suspension has been applied a Opadry final coat is applied.

| Modified realease pellets MRP: | |
| --- | --- |
| Non pareil sugar spheres 30/35 mesh USP/NF | 70% |
| Pharmacoat 603 | 3% |
| Lisdexamphetamine mesylate | 13% |
| Talc USP/NF | 2% |
| Surrelease | 10% |
| Opadry II | 2% |

In a fluid bed drier fitted with Wurster insert, a solution of lisdexamphetamine sulphate and Pharmacoat 603 is sprayed onto non pareils spheres. When the whole amount of suspension has been applied a film of Surrelease is applied. Final surface and color finish is obtained by application of an Opadry film.

15% IRP were mixed with 85% MRP in order to obtain homogenous mix to fill 450 mg capsules that will contain 10 mg of dexamphetamine sulphate and 50 mg of lisdexamphetamine mesylate

EXAMPLE 4

| Presscoated tablets Mantel formulation | |
| --- | --- |
| Hydrogenated castor oil | 55% |
| Anhydrous dicalcium phosphate | 35% |
| Colloidal silica | 0.5% |
| Lactose monohydrate | 9.5% |

Manufacturing process for the mantel: In a jacketed high shear mixer, hydrogenated castor oil, anhydrous dicalcium phosphate and lactose are mixed at a temperature of about 40° C. after cooling the blend is then dry sized on an oscillatory mill and then blend with colloidal silica.

Preparation of press coated tablets; A press coating tablet press is fed with tablets from example 1 to form final press coated tablets having a diameter of 11 mm. Mantel weight is adjusted at 550 mg.

The invention claimed is:

1. A pharmaceutical preparation comprising an amphetamine or a salt thereof and a prodrug of an amphetamine or a salt thereof.

2. The pharmaceutical preparation of claim 1, wherein the amphetamine is dexamphetamine or a salt thereof and the pro-drug is lisdexamphetamine or a salt thereof.

3. The pharmaceutical preparation of claim 2 wherein the amphetamine is dexamphetamine sulphate and the pro-drug is lisdexamphetamine dimesylate.

4. The pharmaceutical preparation of claim 1, wherein the pharmaceutical preparation is in unit dosage form.

5. The pharmaceutical preparation of claim 1, wherein the pharmaceutical preparation is effective to provide a substantially complete release of both amphetamine and amphetamine pro-drug in about 0.5 to 1.0 hour in-vitro in a Type II USP dissolution apparatus in 900 ml 0.1 HCI at 37 degrees centigrade and 50 rpm.

6. The pharmaceutical preparation of claim 5, which provides a dissolution of the amphetamine of from about 5 to 30% within 0.5 hours, about 30 to 70% within 1.0 hours and not less than 80% within 1.5 hours when measured in a Type II USP dissolution apparatus in 900 ml 0.1 at 37 degrees centigrade and 50 rpm.

7. The pharmaceutical preparation of claim 5, which provides for the dissolution of the amphetamine pro-drug of from about 5 to 50% within 5 minutes, about 20 to 70% within 10 minutes and not less than 80% within 20 minutes when measured in a Type II USP dissolution apparatus in 900 ml 0.1 HCI at 37 degrees centigrade and 50 rpm.

8. The pharmaceutical preparation according of claim 1, which provides a mean time to maximum plasma concentration (Tmax) of the amphetamine of about 1 to 12 hours after oral administration, more particularly 1 to 4 hours or 6 to 12 hours after administration.

9. The pharmaceutical preparation of claim 1, which provides a mean plasma concentration (Cmax) of the amphetamine from about 130 to 1400 ng/ml based on a dose of 5 to 50 mg of amphetamine and amphetamine pro-drug delivered to human subjects.

10. The pharmaceutical preparation of claim 1, wherein the amphetamine is selected from the group consisting of 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, fumarate, gluceptate, glucoheptanoate, gluconate, glutamate, glycerophosphate, gly colly larsani late, hemisulfate, heplanoate, hexafluorophosphate, hexanoate, hexylresorcinate, hydrabamine, hydrobromide, hydrochloride, hydroiodide, hydroxynaphthoate, iodide, isethionate, lactate, lactobionate, laurate, laurylsulphonate, malate, maleate, mandelate, mesylate, methanesulfonate, methylbromide, methylnitrate, methylsulfate, mucate, napbthylate, napsylate, nicotinate, nitrate, N-methylglueamine ammonium salt, oleate, oxalate, palmitate, pamoate, pantothenate, pectinate, persulfate, phosphate, phosphateidiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like.

11. The pharmaceutical preparation according to claim 1, wherein the amphetamine pro-drag is lisdexamphetamine dimesylate.

12. The pharmaceutical preparation according to claim 1, comprising lisdexamphetamine dimesylate and dexamphetamine sulphate.

13. The pharmaceutical preparation according to claim 1, wherein amphetamine pro-drug is present in an amount of 18 to 180 mg.

14. The pharmaceutical preparation according to claim 1, wherein the amphetamine is present in an amount of 1 to 50 mg.

15. The pharmaceutical preparation according to claim 1 in the form of an oral dosage form adapted for once-a-day administration.

16. The pharmaceutical preparation according to claim 1, adapted for once-a-day administration to be taken before bed time.

17. A method of treating attention deficit hyperactivity disorder (AMID) in a patient in need of such treatment comprising the step of providing said patient with a pharmaceutical preparation as defined in claim 1.

18. The method of claim 17 wherein the patient is a child aged 6 to 12.

19. The method of claim 17 wherein the patient is an adolescent or an adult.

20. A method of treating fatigue in a patient in need of such treatment comprising the step of administering to said patient a pharmaceutical preparation as defined in any claim 1.

21. The method of claim 20, wherein the fatigue is cancer fatigue.

* * * * *

UNITED STATES PATENT AND TRADEMARK OFFICE
CERTIFICATE OF CORRECTION

| | | |
|---|---|---|
| PATENT NO. | : 8,927,608 B2 | Page 1 of 1 |
| APPLICATION NO. | : 13/578652 | |
| DATED | : January 6, 2015 | |
| INVENTOR(S) | : Guy Vergnault et al. | |

It is certified that error appears in the above-identified patent and that said Letters Patent is hereby corrected as shown below:

In the Claims

At column 18, line number 19, in claim 6, after the number 0.1, please insert --HCl--.

Signed and Sealed this
Seventh Day of April, 2015

Michelle K. Lee
*Director of the United States Patent and Trademark Office*